Figure 1:
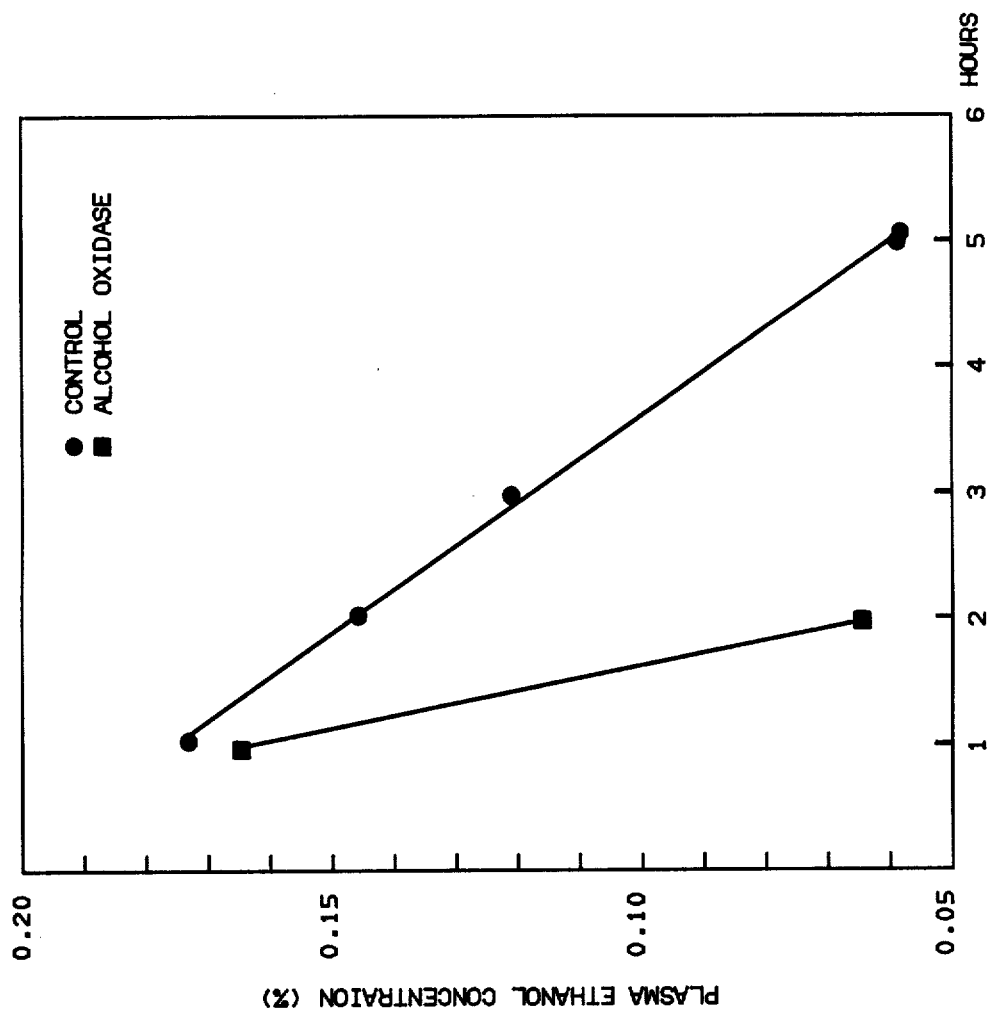

United States Patent [19]

Hopkins

[11] 4,450,153

[45] May 22, 1984

[54] ALCOHOL REMOVAL FROM BLOOD WITH ALCOHOL OXIDASE

[75] Inventor: Thomas R. Hopkins, Bartlesville, Okla.

[73] Assignee: Phillips Petroleum Company, Bartlesville, Okla.

[21] Appl. No.: 429,758

[22] Filed: Sep. 30, 1982

[51] Int. Cl.$^3$ .............................................. A61K 37/48
[52] U.S. Cl. .......................................... 424/94; 604/5
[58] Field of Search ......................................... 424/94

[56] References Cited

U.S. PATENT DOCUMENTS 3,865,726  2/1975  Chibata et al. ........................ 424/94
3,963,613  6/1976  Chibata et al. ...................... 435/283

OTHER PUBLICATIONS

Science Digest–May 1981, p. 109.
Rosenfeld–Science, (Apr. 1981), pp. 24–25.
Westerfeld–American Journal of Clinical Nutrition, vol. 9, (Aug. 1961), pp. 426–431.
Cardemil–Comparitive Biochem. & Physiol., vol. 60B, (1978), pp. 1–7.

*Primary Examiner*—Sam Rosen

[57] ABSTRACT

The level of alcohol content (methanol or ethanol) in blood is reduced by contacting the blood alcohol with the enzyme alcohol oxidase. Injection, extracorporeal shunt (dialysis), and oral administration are contemplated as routes of administration. Suitable compositions for reducing the blood alcohol level are also provided.

39 Claims, 2 Drawing Figures

ALCOHOL REMOVAL FROM BLOOD WITH ALCOHOL OXIDASE

This invention relates to novel compositions and processes to reduce the levels of alcohol present in human blood.

It is known that alcoholism is a wide-spread social problem that has had devastating effects on mankind. Annually, approximately 100,000 people are permanently injured and 30,000 killed due to the effects of alcohol consumption by themselves or other people. In addition, untold millions of dollars worth of property damage are involved in alcohol related accidents. Laws have been passed in an attempt to restrict alcohol consumption and availability, but obviously legislation has far from solved the problem.

Almost all states have by statute defined intoxication with respect to operation of a motor vehicle in terms of a maximum allowable blood alcohol concentration. The most commonly adopted concentration, 0.10% W/V, is now being challenged as being too high. Evidence is mounting to support the contention that a maximum of 0.07% or 0.08% W/V is more consistent with modern studies of alcohol-induced driver impairment. Therefore, methods of reducing the alcohol in blood become increasingly desirable as the legal requirements for intoxication become more stringent.

Ethanol, $CH_3CH_2OH$, or more commonly known as grain alcohol, is a major ingredient in alcoholic beverages. Methanol and other alcohols are also ingredients in impure and improperly prepared alcohol. Both methanol and ethanol have been shown to be toxic when ingested in sufficient quantities. Within the human body, ethanol is metabolized to acetaldehyde, $CH_3CHO$, by the enzyme alcohol dehydrogenase. This enzyme is primarily localized within the liver and kidneys with most of the ethanol conversion carried out in the liver. This enzyme requires a coenzyme called nicotinamide adenine dinucleotide (NAD) in order to catalyze the conversion of ethanol to acetaldehyde.

Acetaldehyde is also a toxic substance and the body disposes of it by metabolizing acetaldehyde to acetic acid in the presence of the enzyme aldehyde dehydrogenase and the coenzyme NAD. Acetic acid can be further broken down into carbon dioxide and water.

The complete metabolism of ethanol can be shown by the following sequence of equations:

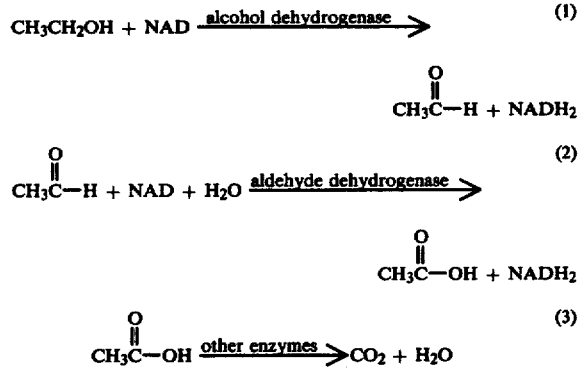

The literature reports that the conversion of ethanol to acetaldehyde as illustrated by equation (1) is much slower than the process of equations (2) and (3), the conversion of acetaldehyde to $CO_2$ and $H_2O$. Therefore, equation (1) is said to be the rate limiting step in the overall process of metabolizing ethanol. Presumably, if the conversion of alcohol to acetaldehyde (reaction 1) was speeded up, the subsequent reactions (2) and (3) could handle the increased load, thus achieving a highly desirable accelerated removal of alcohol from the blood. When administered, the compositions of this invention comprising alcohol oxidase will help to speed up the conversion of ethanol to acetaldehyde, thereby accelerating the removal of alcohol from the blood.

An object of the invention is to provide compositions suitable for the reduction of alcohol in the human blood supply. A further object of this invention is to provide a process for the reduction of human blood alcohol content.

Other aspects, objects, and the several advantages of the present invention will be apparent from an examination of the claims and the detailed description of the invention.

In accordance with one embodiment of this invention, I have discovered that a reduction in the alcohol content of human blood is effected by contacting the blood containing alcohol with the enzyme alcohol oxidase. This contact between the blood alcohol and the enzyme alcohol oxidase can be in any manner or form suitable to reduce or eliminate the alcohol content in human blood.

In accordance with another embodiment of the present invention, novel compositions comprising alcohol oxidase are provided which are effective for reducing the level of alcohol in human blood.

Alcohol oxidase can be purchased commercially from chemical and biological supply houses.

In addition, the alcohol oxidase of this invention can be produced by yeasts of the genus Pichia and those which are genetically and/or taxonomically closely related to Pichia, preferably of the genus Pichia itself, and which are capable of utilizing a feedstock containing methanol as carbon and energy source.

Specific examples of such methanol utilizing Pichia yeasts include

*Pichia pastoris*
*Pichia pinus*
*Pichia trehalophila*
*Pichia molischiana*

Two exemplary strains of suitable yeasts of the species *Pichia pastoris* have been deposited with the U.S. Department of Agriculture, Agriculture Research Service, Northern Regional Research Laboratories of Peoria, Ill., and have received the numerical designations NRRL Y-11430 and Y-11431.

According to the present invention, a selected species of methanol competent Pichia-type yeast, such as *Pichia pastoris* is cultured under aerobic aqueous fermentation conditions using methanol or a combination of methanol and other selected organic compounds as the carbon and energy source. Preferably the methanol is supplied under conditions such that methanol is the growth-limiting factor. The methanol limiting conditions are defined for purposes of this disclosure as a concentration of methanol which is the minimal concentration which results in a maximum growth rate for a given set of fermentation culture conditions. Preferably fermentation is conducted under high cell density conditions, i.e., so that cell density is 100 grams or greater on a dry weight basis per liter of ferment. The selected yeast is grown in a batch or continuous process in the presence of oxygen, methanol, and an assimilable source of nitrogen. Various types of fermentation processes and apparatuses known in the art can be utilized. For example, a foam-type fermenter such as described in U.S. Pat. No. 3,982,998, or other suitable fermenter can be used.

Oxygen can be supplied to the fermenter as such, or in the form of air or oxygen-enriched air, in a range of pressures from such as about 0.1 atm to 100 atm, as is known in the art. The assimilable source of nitrogen for the fermentation can be any organic or inorganic nitrogen containing compound which provides nitrogen in a form suitable for metabolic utilization by the microorganisms. Suitable organic nitrogen sources include, for example, proteins, amino acids, urea, and the like. Suitable inorganic nitrogen sources include, for example, ammonia, ammonium hydroxide, ammonium nitrate, and the like. The presently preferred nitrogen sources include ammonia and ammonium hydroxide for convenience and availability.

The pH range in the aqueous microbial ferment should be in the range of about 3 to 7, more preferably and usually about 3.5 to 5.5. Preferences of certain microorganisms for a pH range are dependent to some extent on the medium employed, as well as on the particular microorganism, and thus may change somewhat with change in medium as can be readily determined by those skilled in the art.

Sufficient water is maintained in the fermentation means so as to provide for the particular requirements of the microorganism employed as well as to provide a carrier fluid for water soluble nutrients. Minerals, growth factors, vitamins, and the like, generally are added in amounts which vary according to the strain of microorganism utilized and the selected culture conditions, and are known to those skilled in the art or are readily determinable by them. A typical nutrient medium is set forth below in Example I.

The growth of the microorganism is sensitive to the operating temperature of the fermenter and each particular strain of microorganism has an optimum temperature for growth. Exemplary fermentation temperatures are in the range of about 20° C. to about 65° C. The temperature selected will generally depend upon the microorganism employed in the process since each one will have a somewhat different temperature/growth rate relationship.

Fermentation pressures are generally within the range of about 0.1 to about 100 atmospheres, more usually about 1 to about 30 atmospheres, and more preferably about 1 to about 5 atmospheres since the higher pressures result in a greater level of dissolved oxygen in the aqueous medium and usually higher cell productivities.

ALCOHOL OXIDASE ISOLATION

A fluid is prepared which is an aqueous suspension containing cells of the selected microorganism. The aqueous fluid can be fermenter effluent which can be used directly, or preferably after adjusting the pH as described below. Alternatively the suspended microorganism cells can be initially separated from the fermentation medium, for example, by centrifugation or by filtration through filters having a pore size less than the size of the individual cells, and subsequently resuspended in a convenient volume of water or of an appropriate aqueous buffer, for example $KH_2PO_4/Na_2HPO_4$ buffer at 0.2 M. The cell density in the aqueous suspension must be greater than a minimum crystallization density. Satisfactory results are obtained if the fluid cell density is greater than about 75 grams on a dry weight basis per liter of fluids. In addition satisfactory results are obtained if the fermenter effluent, where it is to be used as the fluid, is first adjusted to a pH of such as about 7.5 by addition of a base such as ammonium hydroxide, sodium hydroxide, and the like. The pH is not considered critical, however and the pH of the aqueous suspension need not be adjusted prior to homogenization. However, it is considered preferable to adjust the pH broadly in the range of about 6–9 since in this range the enzyme is active and stable.

The cell-containing fluid can be homogenized by suitable means known in the art. For example, fermenter effluent containing yeast grown on methanol can be adjusted to a pH of about 7.5 and homogenized at a high cell density concentration such as 100–120 grams biomass (dry weight)/liter using a Dynomill ® Model KDL using a 0.6 liter vessel filled to 70–90% volume with 0.5 mm diameter spherical grinding media in a continuous operation at 5° to 30° C. using belt combination #3 and a flow of 20–30 mL/hr. The homogenate solids are separated from the homogenate to produce a crude solution containing alcohol oxidase as a soluble component. For example, the homogenate solids can be removed by centrifugation to yield a cell-free supernatant. Alternatively the solids can be removed by filtration through filters having a suitable pore size, followed by pH adjustment if desired. For further purification steps such as recovery of crystalline alcohol oxidase, the pH can be adjusted in the range of 5.75 to 6.75 as desired, for example, to pH 6.5.

PREPARATION OF CRYSTALLINE ALCOHOL OXIDASE

The crude solution containing the soluble alcohol oxidase can be treated to recover crystalline alcohol oxidase either in more concentrated solid form by such as fractional precipitation with ammonium sulfate, or more desirably and preferably as the potent crystalline form exhibiting highest activity by treatment under dialysis conditions either by conventional dialysis modes or by applying ultra-filtration to increase the rate of recovery.

In dialysis, the crude solution containing the soluble alcohol oxidase is dialyzed against a dialysis medium across a membrane impermeable to alcohol oxidase but permeable to water, buffer salts, and other low molecular weight molecules. The crude solution is prepared by homogenizing an aqueous fluid having a cell density effective for crystallization of alcohol oxidase when the solution attains a recovery range solution condition as herein described. Satisfactory crystallization has been observed where the effective cell density prior to homogenization was about 75 grams (on a dry weight basis) per liter of aqueous fluid or more. Crystallization is also expected to occur at even lower effective cell densities although the amount of crystalline alcohol oxidase recovered is less. Below an empirically determinable minimum cell density (minimum crystallization density) essentially no crystalline alcohol oxidase is recovered.

The type of membrane used is not considered critical and any suitable membrane may be used. For example, commercially available cellulose acetate dialysis tubing can be used to form dialysis bags or otherwise used, or hollow fiber dialysis cells can be used. The alcohol oxidase containing solution is dialyzed against a dialysis medium, for example water or a buffer solution, to achieve a recovery range solution on the enzyme side of the membrane having an ionic strength in a recovery range of between 0.05 M and 0.01 M thereby effecting precipitation of an electrophoretically homogeneous crystalline alcohol oxidase.

The dialysis medium can be any medium whereby during dialysis the molar ionic strength of the solution on the enzyme side of the membrane passes through at least a portion of the recovery range. For example, if the crude solution containing alcohol oxidase has a molar ionic strength of 0.2 M, the dialysis medium can be a suitable volume of distilled water. The volume of fluid against which the enzyme is dialyzed is not considered critical so long as the ionic strength on the enzyme side of the membrane passes through at least a portion of the recovery range.

During dialysis, the pH of the alcohol oxidase containing solution should be maintained in the range of about 5.75 to about 6.75 by use of a suitable buffer system. A suitable buffer system comprises, for example, potassium dihydrogen phosphate and disodium hydrogen phosphate. Preferably the pH range is from about 6.0 to about 6.5 for recovery of maximum amounts of crystalline alcohol oxidase. As shown in the example below, good crystallization of the alcohol oxidase has been observed within the broad pH range, and the narrow range represents a presently preferred pH range to achieve minimum solubility of the enzyme.

The alcohol oxidase has minimum solubility under these conditions in solutions of 0.02 M ionic strength at pH 6.0 to 6.25. Consequently, optimum crystallization is achieved by planning the dialysis to obtain these conditions. Good crystallization can be achieved by exhaustive dialysis of the enzyme containing solution against large volumes of buffers meeting the above conditions. Alternatively, the dialysis system can be designed to achieve optimal crystallization conditions either at equilibrium or at a point in time after the start of dialysis. For example, a crude enzyme solution having an ionic strength of 0.2 M at pH 6.25 can be dialyzed against a nine-fold excess of distilled water (relative to the volume of the crude enzyme solution). At equilibration, the ionic strength of the crude enzyme solution will be 0.02 M and crystallization will occur. Such a method has the disadvantage that a relatively long period of time is required for equilibration to occur.

On the other hand, if the crude enzyme solution has a molar ionic strength of, for example, 0.1 M, dialysis against a nineteen-fold excess of distilled water (relative to the volume of the crude enzyme solution) to equilibration will result in a solution having 0.005 M ionic strength and crystals formed will tend to redissolve since the equilibrium ionic strength is outside the recovery range. However, the crystals will form after a relatively shorter dialysis time and may then be removed and recovered before system equilibration and redissolution.

The dialysis can be safely carried out at temperatures in the range of from about 4° C. to about 40° C. Sufficient time, generally more than one hour, and preferably 18 hours, or more, must be allowed for crystallization to occur.

At the end of dialysis, the alcohol oxidase is present in the dialysis bag as a crystalline solid. The crystalline alcohol oxidase can be readily separated from the dialysis medium, such as by decanting the liquid in the dialysis bag from the solid crystals. The moist crystals can be further processed as desired for storage. For example, the crystal slurry can be frozen, dried at low temperature, or can be dissolved in water or more preferably in a phosphate buffer. Stabilizer compounds known to stabilize enzyme solutions against denaturation and loss of enzymatic activity can be added, such as 50 percent sucrose or 0.02 weight percent sodium azide.

It is suitable to store the prepared enzyme at temperatures in the range of about −70° C. to 40° C. More preferably, the enzyme is stored at temperatures in the range of about −40° C. to 24° C. Only minimal loss of activity has been found to occur when the enzyme is stored at 4° C. in 0.1 M phosphate buffer at pH 7.5, and with 0.02% sodium azide to inhibit microorganism growth.

In the process of preparing alcohol oxidase from Pichia microorganisms, a crystalline solid is formed during dialysis of the crude enzyme solution and no further purification steps have been found necessary.

INJECTION

In this embodiment of the present invention alcohol oxidase is administered through the route of direct injection into the human body. Preferably, alcohol oxidase will be administered either intravenously, intramuscularly, or intraperitonealy. These three particular routes are most commonly used for the administration of any type of solution into the human body when injection is employed. Intravenous injection is preferred when it is desirable to rapidly disperse the injection solution throughout the body. In contrast, intramuscular or intraperitoneal injection are preferred when a slower dispersal of the injection solution is desired.

In the practice of this embodiment of the present invention, a composition comprising alcohol oxidase is injected into the body. This composition will take the form of a sterile solution of alcohol oxidase in water. Sodium chloride, glucose, or the like may be added in amounts sufficient to render the resulting alcohol oxidase solution isotonic.

An isotonic buffer solution is desirable because it serves the function of maintaining protein stability during storage of the injection solution. It also helps to prevent hemolysis and circulatory shock upon injection. The concentration of alcohol oxidase in solution can be up to 150 mg of alcohol oxidase/mL of isotonic buffer solution.

When injected, alcohol oxidase should be administered in an amount sufficient to reduce the amount of alcohol present in the human blood to the desired level. In general, alcohol oxidase should be administered in an amount in the range of from about 1 to about 100 mg of alcohol oxidase (AO) as a solution per kg of body weight of the recipient. The precise range of AO concentration will vary with the exact site of injection. Higher amounts of AO are required for injection into either the muscular or interperitoneal region as compared to the veins because in these two areas the enzyme will be released into the blood stream containing the alcohol over a longer period of time.

Since alcohol oxidase acts as a biological catalyst and not a reagent which would react stoichiometrically with its alcohol substrate, it is not expected that the exact dosage of alcohol oxidase administered will vary much with the amount of alcohol present in the user's blood. The time for alcohol clearance is the important factor in this enzyme application and this will usually require maximum dosage, even if the user is only marginally over the legal limit in blood alcohol concentration.

In the sterile alcohol oxidase injection solution, the presence of other substances as discussed below is preferred in some instances.

In the practice of the present invention, it is believed that the dosage levels of the above preferred substances in the alcohol oxidase injection solution are not critical. It is only desirable that they be present in amounts sufficient enough to satisfy their particular function in the injection solution.

The alcohol oxidase could be injected in the form of a microencapsulated enzyme. The use of semipermeable membranes allows control of the environment around the enzyme, thus prolonging the lifetime of the enzyme and avoiding contact with external macromolecules like antibodies.

Attachment of alcohol oxidase to substances such as dextran and polyethylene glycol which suppresses immunological reactions and prolongs the lifetime of the enzyme in the circulation is desirable. Soluble conjugates of enzyme with dextran and polyethylene glycol can be prepared by activating either suppressing agent with cyanuric bromide or chloride. The activated agent is then covalently bound to the alcohol oxidase. The use of dextran as a suppressing agent for immunological reactions is disclosed in *The Journal of Applied Biochemistry* 1, 88–94 (1979) and polyethylene glycol is disclosed in *Enzyme Engineering* 4, pp. 169–173 (1978).

The injected alcohol oxidase solution can be admixed with an oxygen carrying substance such as an aqueous emulsion of perfluorodecalin and perfluorotripropylamine or other oxygen-carrying blood replacement solutions as are known in the art and are commercially available. This is desirable because reaction of alcohol oxidase with alcohol consumes oxygen (one mole per mole of alcohol consumed) as shown in Equation 4.

$$CH_3CH_2OH + O_2 \xrightarrow{\text{alcohol oxidase}} CH_3CHO + H_2O_2 \quad (4)$$

The introduction of additional oxygen to the bloodstream will minimize oxygen depletion at the site of rapid alcohol removal by the action of alcohol oxidase.

The addition of antioxidants such as ascorbic acid, ascorbyl palmitate, monothioglycerol and the like are desirable to aid stability of the enzyme solution and to reduce the likelihood of free radical processes (which can consume $O_2$) occurring upon reaction of the enzyme alcohol oxidase with high levels of blood alcohol.

The presence of the vitamin niacin is also desirable in an alcohol oxidase injection solution. This is because niacin is a precursor for the co-factor NAD which participates in the enzyme catalyzed breakdown of alcohol in human blood.

EXTRACORPOREAL SHUNT (DIALYSIS)

In this embodiment of the present invention, the blood containing alcohol from a person could be shunted through a renal dialysis unit consisting of an external column of a bed of immobilized sterile alcohol oxidase solution in water or isotonic saline solution. This precludes physical and immunological problems because the enzyme protein is not in direct contact with the circulatory system inside the human body where immunological agents can be formed.

The procedure contemplated in the process of this aspect of the present invention is that of any standard or conventional renal dialysis process. To rapidly reduce the alcohol level in the blood, the use of enzymes (such as alcohol oxidase) in a dialysis machine will function to hasten the break down of the alcohol eventually to $CO_2$ and $H_2O$ according to equations (1), (2), (3) and (4), detailed above.

The blood is circulated through dialysis type membranes or tubes such as hollow fibers and capillary tubes in which the fluid flowing countercurrent to the blood flow is composed of aerated saline isotonic solution containing the enzyme alcohol oxidase. The blood containing alcohol is contacted with alcohol oxidase for a time sufficient to reduce the level of the alcohol in the blood stream. Generally, alcohol oxidase should be administered in an amount of 1–200 mg of alcohol oxidase per mL of injection solution. The alcohol from the blood passes through the membrane into the oxygenated alcohol oxidase which converts the ethanol into acetaldehyde and $H_2O_2$. It may also be desirable to have present catalase to convert the $H_2O_2$ to $H_2O$ and $O_2$. Further, the acetaldehyde can be either enzymatically or chemically converted (such as to acetic acid by acetaldehyde dehydrogenase and NAD) or trapped in such a manner that it cannot return to the blood (i.e. use of insoluble substances such as activated charcoal or resins which can bind acetaldehyde).

ORAL CONSUMPTION

In this embodiment of the present invention, alcohol oxidase is administered orally. Through oral administration, a pill or tonic solution containing alcohol oxidase is ingested by the intended recipient. Alcohol oxidase, when placed in the intestinal tract, will then rapidly oxidize its alcohol substrate which will have diffused through the immense surface area of the intestinal illium from the capillary blood supply of the intestine into the gut where it will be oxidatively broken down.

The pill or tonic solution should contain alcohol oxidase in an amount sufficient to remove the alcohol from the blood stream to the desired level. Generally, in a tablet or pill form alcohol oxidase should be present in an amount ranging from about 1 mg to 1 g per tablet (pill). If the enzyme is administered in the form of a tonic, i.e. alcohol oxidase in an aqueous solution which can be consumed orally, then alcohol oxidase should be present in an amount from about 1–200 mg protein/mL of tonic solution.

In the practice of the present invention, from about 1–5 tablets containing alcohol oxidase are contemplated for oral administration per recipient in order to reduce the level of alcohol to desired levels. If an oral tonic is given, then from 1 to 50 mL of the tonic are contemplated for administration to achieve alcohol reduction to desired levels.

By this embodiment of the invention, the tablet or pill will be in the compressed form such form being well known to those skilled in the art. The compressed form offers the advantage of being capable of rapid, mass production.

The presence of a diluent or filler in a tablet comprising alcohol oxidase would be desirable as it aids in cohesiveness to the pill form and also serves as a filler when the amount of alcohol oxidase present is small or is sufficiently difficult to compress into a tablet. Conventional tablet diluents include but are not limited to lactose, starch, dibasic calcium phosphate and calcium sulfate. If the pill or tablet is to be chewable, then sucrose, mannitol and sorbitol would be appropriate diluents or fillers.

Additionally, the use of a binder would serve to give adhesiveness to the tablet beyond what is already given by the use of a diluent. Conventional tablet binders include but are not limited to acacia, gelatin, sucrose, povidone, methyl cellulose, alginic acid, guar gum, or hydrolyzed starch paste.

The use of disintegrating agents are also preferred as they assist in the fragmentation of the pill after administration. Common disintegrating agents used in the art include starch, alginic acid, microcrystalline cellulose, cross-linked providone and colloidal silicates.

During the production of compressed tablets in manufacturing processes, they will frequently adhere to dies and punches. Therefore, the presence of a lubricant in a pill containing alcohol oxidase is highly desirable to reduce friction during the compression and ejection cycle of its manufacture. Common lubricants include polyethylene glycols, lauryl sulfate, Group IA and Group IIA metal stearate salts, stearic acid and hydrogenated vegetable oils.

The amounts of the above substances in the tablet or tonic (as in the case of niacin) is not thought to be critical in the practice of the present invention. Rather, it is only desirable that they be present in an amount sufficient to satisfy their particular function.

Because the acidity of the stomach would irreversibly inactivate alcohol oxidase, in a preferred embodiment of this invention the pill may be treated with any substance suitable to slow down this occurrence. Typically the treatment consists of coating the alcohol oxidase with the substance in any suitable fashion so as to diminish the alcohol oxidase's susceptability to acid attack. Typical enteric coating substances with which the enzyme can be protected include polysaccharides such as gum agar, carbon bean gum, agar-agar, Na-alginate, carrageenan, gluten, acetophthalic resins, and cationic acrylic polymerizates.

The following examples further illustrate the invention.

EXAMPLE I

In a continuous aerobic fermentation process, methanol and an aqueous mineral salts medium in a volume ratio of about 40 to 60, respectively, were fed individually to a fermenter, inoculated with the yeast species *Pichia pastoris* NRRL Y-11430, at a rate so that methanol is the growth-limiting factor. The fermenter was a 1500-liter foam-filled fermenter with a liquid volume of about 610 liters, with automatic pH, temperature, and level control. Agitation was provided by two conventional paddle-type turbines driven at 1000 RPM. The aeration rate was about 4 volumes of air (at about 38 psig and about 25° C.) per volume of ferment in the fermenter per minute. Anhydrous ammonia was added at such a rate as to maintain the pH of the fermentation mixture at about 3.5.

The aqueous mineral salts medium was prepared by mixing, with each liter of tap water, 15.86 mL 75 percent $H_3PO_4$, 9.53 g $K_2SO_4$, 7.8 g $MgSO_4.7H_2O$, 0.6 g $CaCl_2.2H_2O$, and 2.6 g 85 percent KOH. The trace mineral solution plus biotin was fed separately via the methanol stream at a rate of 10 mL per liter of methanol. The trace mineral solution plus biotin was prepared by mixing 780 mL of a trace mineral solution, 20 mL water, 200 mL methanol and 0.032 g biotin.

The trace mineral solution was prepared by mixing, for each liter of solution, 65 g $FeSO_4.7H_2O$, 20 g $ZnSO_4.7H_2O$, 3.0 g $MnSO_4.H_2O$, 6.0 g $CuSO_4.5H_2O$, 5.0 mL conc. $H_2SO_4$, and sufficient deionized water to make 1 liter of solution.

The aqueous mineral salts medium was fed at a rate of 31.5 liters per hour and the methanol at a rate of 21 liters per hour.

The fermentation was conducted at about 30° C. and about 38 psig pressure, with a retention time of 11.6 hours.

For analytical purposes, the resulting yeast cells were separated from the fermentation effluent (ferment) by centrifugation, washed by suspension in water and recentrifugation, dried overnight at 100° C., and weighed. On a dried basis, the yield of yeast cells typically was about 40.6 g per 100 g of methanol feed. The cell density typically was about 128.4 g of cells per liter of fermenter effluent. The total solids content of the ferment typically was about 134.7 g per liter, cells plus dissolved solids. A portion of the fermenter effluent was frozen and stored. In addition, a portion of the fermenter effluent was removed and adjusted to pH 7.5 with ammonium hydroxide, and was homogenized on a Dynomill Model KDL using a 0.6 liter vessel in a continuous operation at 30° using belt combination #3 and a flow of 20–30 mL/hr. The beads in the mill were lead free glass beads with a diameter of 0.3–0.5 mm. The resulting homogenate was centrifuged at 5° C. and 20,000×g for 30 minutes to yield a cell-free supernatant.

Six 130 mL portions of the supernatant were placed in cellulose acetate dialysis bags and dialyzed at 5° C. against about 8 liters of distilled water. After 4 days, the aqueous phase of each bag was decanted. The solids remaining in the bags consisted of two types of solid. The thin upper white layer was carefully removed and discarded. The bottom solid was brown-yellow and was the alcohol oxidase.

A sample of the solid alcohol oxidase was examined by SDS gel electrophoresis and a single band was observed indicating a homogeneously pure enzyme.

The results of this example demonstrate the process utilized for the preparation and isolation of pure crystalline alcohol oxidase from *Pichia pastoris*.

EXAMPLE II

Ethanol (25 μL) was added to 10 mL samples of (1) whole blood; (2) blood serum; and (3) phosphate buffer (0.05 M, pH 7.5). Approximately 2 mg purified alcohol oxidase, prepared as described above, was added to each sample to yield a final concentration of 2.5 units/mL. Samples were monitored over several hours by gas liquid chromatography for ethanol and acetaldehyde content.

TABLE I

| Time, min | Ethanol Peak Height | | | Acetaldehyde Peak Height | | |
|---|---|---|---|---|---|---|
| (Sample) | (1) | (2) | (3) | (1) | (2) | (3) |
| 0 | 62 | 55 | 45 | 0 | 0 | 0 |
| 10 | 55 | 46 | ND* | 2.5 | 7.5 | ND |
| 30 | 56 | 42.5 | 39 | 7.5 | 16.0 | 9.5 |
| 60 | 42.5 | 34 | 35 | 14 | 24.5 | 15 |
| 180 | 17 | 7.5 | 24 | 43 | 44 | 56 |
| 300 | 2.5 | 4.5 | 18 | 47 | 30 | 66 |

*ND = not determined.

This example demonstrates the activity of alcohol oxidase in whole blood and blood serum samples for the reduction of blood alcohol concentration. Note that the rate of alcohol removal in whole blood is somewhat greater than in buffer.

EXAMPLE III

In an in vivo experiment, rats were anesthetized with (1000 mg/kg) urethan. Each animal's femoral vein and artery of one hind limb were cannulated with PE-50 tubing. These cannulae were used for the administration of alcohol oxidase and for the collection of blood samples for plasma ethanol analysis. Body temperature was maintained at 37° C. with a temperature regulating device. The animals were dosed with ethanol at 3.5 g/kg body weight. Ethanol was administered by oral gavage as a 45% solution in saline. This dose of ethanol produced a blood level of 0.1 to 0.2% by 1 hour post administration. The animals were dosed with alcohol oxidase intravenously one hour following ethanol administration. Blood ethanol concentrations were determined by GLC.

The effect of alcohol oxidase at a dose of 50 mg/kg body weight on ethanol elimination is shown in FIG. 1.

The data presented in FIG. 1 demonstrate that alcohol oxidase markedly increased the elimination of ethanol from the blood. The half-life of ethanol was reduced from a control value of 2.75 hours to 0.8 hours. This indicates that the metabolism of ethanol was increased greater than three fold by the administration of alcohol oxidase.

EXAMPLE IV

In another in vivo experiment, rabbits (both sexes) were anesthetized by intraperitoneal injection of sodium thiamylal; a suitable dose level of 2% solution was determined empirically to be 2.5 mL/kg. Anesthetic was administered approximately every 30 minutes. The physical condition of the anesthetized experimental animals was closely watched and vital signs monitored periodically.

A 20 gauge cannula for collection of blood was inserted through the femoral vein into the abdominal vena cava. A 20 mm length of surgical tubing was inserted through a small incision in the vessel. The distal portion of the vein was tied off and the proximal portion tied around the cannula to avoid loss of blood. This tubing was kept patent with a solution of sodium heparin (1000 U).

Ethanol (dose=3.5 g/kg) was administered orally through a polyethylene tube inserted deep in the stomach.

Alcohol oxidase at a dose of 10 mg/kg was administered intravenously 15 minutes after the ethanol. Blood samples were taken every 15 minutes for the first two hours after dosing, then hourly for the next two hours.

The ethanol concentration in the rabbit blood samples was analyzed according to a standard forensic alcohol analysis method. A 50 μL aliquot of each blood samples was diluted with 1.6 mL of distilled water containing 0.25 μL/mL of isopropanol as an internal standard. A series of standards was prepared by adding known quantities of ethanol to 1 mL rabbit blood. The ethanol analysis was performed with a Hewlett-Packard 5731A gas chromatograph equipped with a flame ionization detector. A 6'×⅛" glass column, packed with 1% SP-1000 on Carbopack B (60/80) was used at an isothermal temperature of 75° C. The injection port detector temperatures were 100° C. and 200° C. respectively.

The limit of detection was 0.01 mg for ethanol per 50 μL volume of the blood sample.

Figure 2:
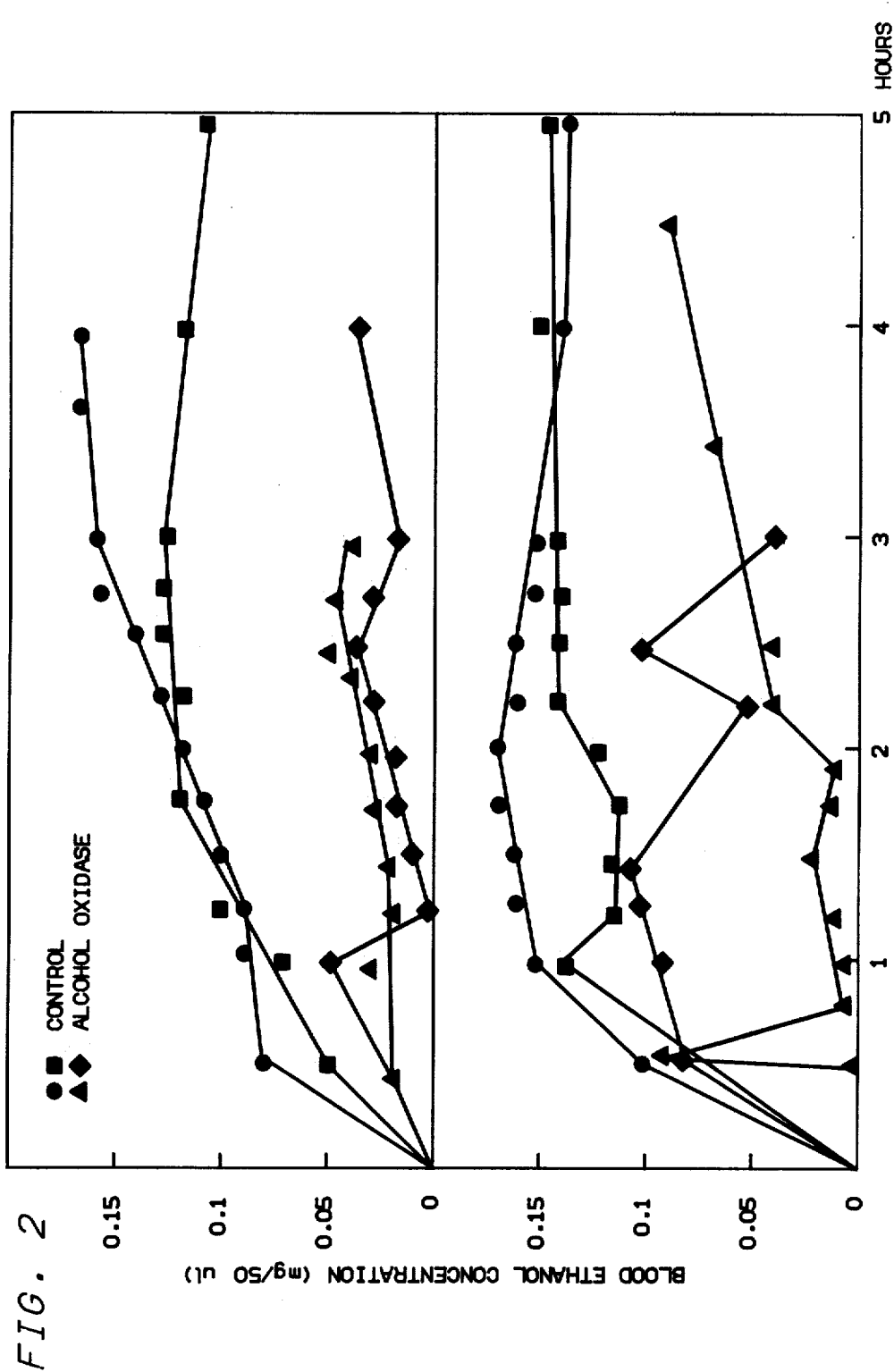

The data for 8 animals (4 male and 4 female) are shown in Table II below and in graphical form in FIG. 2.

TABLE II

| Animal # | Sample # | Hrs. After EtOH Admin. | [EtOH] mg/50 μl |
|---|---|---|---|
| Control Group: Ethanol | | | |
| 1 (Female) | 0 | −0.18 | <0.0 |
|  | 1 | 0.5 | 0.8 |
|  | 2 | 1.0 | 0.09 |
|  | 3 | 1.25 | 0.1 |
|  | 4 | 1.5 | 0.11 |
|  | 5 | 1.75 | 0.11 |
|  | 6 | 2 | 0.12 |
|  | 7 | 2.25 | 0.14 |
|  | 8 | 2.5 | 0.14 |
|  | 9 | 2.75 | 0.14 |
|  | 10 | 3.0 | 0.14 |
|  | 11 | 4.0 | 0.15 |
|  | 12 | 5.0 | 0.14 |
| 2 (Female) | 0 | −0.38 | <0.01 |
|  | 1 | 0.5 | 0.1 |
|  | 2 | 1.0 | 0.15 |
|  | 3 | 1.25 | 0.16 |
|  | 4 | 1.5 | 0.16 |
|  | 5 | 1.75 | 0.17 |
|  | 6 | 2.0 | 0.17 |
|  | 7 | 2.25 | 0.16 |
|  | 8 | 2.5 | 0.16 |
|  | 9 | 2.75 | 0.15 |
|  | 10 | 3.0 | 0.15 |
|  | 11 | 4.0 | 0.14 |
|  | 12 | 5.0 | 0.14 |
| 3 (Male) | 0 | −0.25 | <0.01 |
|  | 1 | 0.5 | 0.08 |
|  | 2 | 1.0 | 0.09 |
|  | 3 | 1.26 | 0.09 |
|  | 4 | 1.5 | 0.1 |
|  | 5 | 1.75 | 0.11 |
|  | 6 | 2 | 0.12 |
|  | 7 | 2.25 | 0.13 |
|  | 8 | 2.55 | 0.14 |
|  | 9 | 2.75 | 0.16 |
|  | 10 | 3 | 0.16 |
|  | 11 | 3.63 | 0.17 |
|  | 12 | 4 | 0.17 |
| 4 (Male) | 0 | 0 | <0.01 |
|  | 1 | 0.5 | 0.05 |
|  | 2 | 1 | 0.08 |
|  | 3 | 1.25 | 0.1 |
|  | 4 | 1.75 | 0.12 |
|  | 5 | 2.0 | 0.12 |
|  | 6 | 2.25 | 0.12 |
|  | 7 | 2.5 | 0.13 |
|  | 8 | 2.75 | 0.13 |
|  | 9 | 3 | 0.13 |
|  | 10 | 4 | 0.12 |
|  | 11 | 5 | 0.11 |
| Experimental Group: Ethanol + Alcohol Oxidase (AO) | | | |
| 5 (Female) | 0 | −1.17 | <0.01 |
|  | 1 | N.D. |  |
|  | 2 | 0.95 | 0.11 |
|  | AO | 0.55 | — |
|  | 3 | 1.2 | 0.11 |
|  | 4 | 1.45 | 0.11 |
|  | 5 | 1.72 | 0.09 |
|  | 6 | 1.97 | 0.07 |
|  | 7 | 2.22 | 0.05 |
|  | 8 | 2.47 | 0.1 |
|  | 9 | 3.0 | 0.04 |
|  | Death | 3.25 |  |
| 6 (Female) | 0 | −0.11 | N.D. |
|  | 1 | 0.3 | <0.01 |
|  | 2 | 0.52 | 0.09 |
|  | AO | 1.0 | — |
|  | 3 | 0.8 | <0.01 |
|  | 4 | 1 | <0.01 |
|  | 5 | 1.22 | 0.01 |
|  | 6 | 1.5 | 0.02 |

TABLE II-continued

| Animal # | Sample # | Hrs. After EtOH Admin. | [EtOH] mg/50 μl |
|---|---|---|---|
| | 7 | 1.77 | 0.01 |
| | 8 | 1.93 | 0.03 |
| | 9 | 2.22 | 0.04 |
| | 10 | 2.5 | 0.04 |
| | 11 | 3.47 | 0.07 |
| | 12 | 4.47 | 0.09 |
| 7 (Male) | 0 | −0.36 | <0.01 |
| | 1 | 0.46 | 0.02 |
| | 2 | 0.96 | 0.03 |
| | AO | 1.0 | — |
| | 3 | 1.22 | 0.02 |
| | 4 | 1.47 | 0.02 |
| | 5 | 1.72 | 0.03 |
| | 6 | 1.97 | 0.03 |
| | 7 | 2.33 | 0.04 |
| | 8 | 2.47 | 0.05 |
| | 9 | 2.72 | 0.05 |
| | 10 | 2.97 | 0.04 |
| | Death | 2.98 | |
| 8 (Male) | 0 | −0.23 | <0.01 |
| | 1 | 0.5 | 0.02 |
| | 2 | 0.98 | 0.05 |
| | AO | 1.0 | — |
| | 3 | 1.25 | <0.01 |
| | 4 | 1.5 | 0.01 |
| | 5 | 1.75 | 0.02 |
| | 6 | 2 | 0.02 |
| | 7 | 2.25 | 0.03 |
| | 8 | 2.5 | 0.04 |
| | 9 | 2.75 | 0.03 |
| | 10 | 3 | 0.02 |
| | 11 | 3.5 | <0.01 |
| | 12 | 4.0 | 0.03 |

N.D. = Not Determined.

The experimental data indicated that the blood ethanol concentration in rabbits treated with 10 mg/kg body weight alcohol oxidase was reduced in comparison with the blood ethanol concentration from rabbits treated with only ethanol. The mean ethanol concentration for all data points from the ethanol and alcohol oxidase group (x=0.042; n=42) and from the ethanol control group (x=0.127; n=47) indicate an approximate three-fold reduction of ethanol concentration in the presence of alcohol oxidase.

In addition, the above data show that animals which are injected with alcohol oxidase having relatively large concentrations of alcohol in their blood, may ultimately die under the stressed condition employed for these studies. Therefore, caution is urged in injection of alcohol oxidase where higher levels of alcohol are present.

In separate experiments, a large dose of alcohol oxidase administered to rats or rabbits *not* containing ethanol in their circulatory system had no measurable effect on the animal. Alcohol oxidase, a natural catalyst, is not harmful to the test animal.

EXAMPLE V

The effectiveness of an extracorporeal shunt (renal dialysis device) containing alcohol oxidase to remove alcohol from whole blood was demonstrated in the following in vitro experiment. Pooled whole human blood (treated with ethylene diaminetetraacetic acid as an anticoagulant) was made 0.2 vol % in ethanol and passed through a Spectropor HF (hollow fiber bundle of 176 fibers per unit, molecular weight cutoff 5000, working volume 2 mL) at varying flow rates. A solution of alcohol oxidase in isotonic phosphate buffer plus 5 percent glucose solution surrounded the hollow fiber bundles through which the blood passed. The residence time of the ethanol containing blood with the enzyme solution was varied from 0.2 to 10 minutes. After the blood exited the hollow fiber bundle, samples were taken to measure alcohol content. The results are shown in Table III.

TABLE III

| Blood Ethanol Concentration, V/V | Contact Time, Min. | % Ethanol Removal |
|---|---|---|
| 0.2 | 0 | — |
| 0.18 | 0.2 | 10 |
| 0.13 | 0.4 | 35 |
| 0.125 | 0.8 | 37.5 |
| 0.1 | 2 | 50 |
| 0.07 | 4 | 65 |

The above data show that the blood alcohol was reduced 50 percent within a 2 minute contact time.

Reasonable variations and modifications are possible within the scope of the present invention without departing from the spirit thereof.

I claim:

1. A process for reducing the alcohol content of human blood comprising contacting said alcohol with the enzyme alcohol oxidase wherein said alcohol oxidase, present in an injectable solution, is injected into the human body in the amount from about 1 to about 100 mg/Kg of body weight of the recipient.

2. A process according to claim 1 wherein said alcohol is ethanol or methanol.

3. A process according to claim 1 wherein said alcohol oxidase is present in either an aqueous or isotonic saline solution.

4. A process according to claim 3 wherein said alcohol oxidase is admixed with an oxygen carrier.

5. A process according to claim 4 wherein said oxygen carrier is an aqueous emulsion of perfluorodecalin and perfluorotripropylamine.

6. A process according to claim 4 wherein said alcohol oxidase is combined with an antioxidant.

7. A process according to claim 6 wherein said antioxidant is one of ascorbic acid, ascorbyl palmitate, and monothioglycerol.

8. A process according to claim 4 wherein said alcohol oxidase is administered by intravenous injection.

9. A process according to claim 4 wherein said alcohol oxidase is administered by intramuscular injection.

10. A process according to claim 4 wherein said alcohol oxidase is administered by intraperitoneal injection.

11. A process according to claim 4 wherein niacin is present in the injection solution.

12. A process according to claim 4 wherein said alcohol oxidase is attached to either dextran or a polyethylene glycol.

13. A process according to claim 4 wherein said alcohol oxidase is in a microencapsulated form.

14. A process for reducing the alcohol content of human blood wherein said blood is contacted by renal dialysis with said alcohol oxidase, present in sterile solution, in an amount of from 1-200 mg of alcohol oxidase/Kg of body weight of the recipient.

15. A process according to claim 14 wherein said blood is contacted with said alcohol oxidase for a time sufficient to reduce the level of said alcohol in the blood stream.

16. A process for reducing the alcohol content of human blood wherein alcohol oxidase is administered orally to a recipient as a pill or tablet containing an amount of alcohol oxidase from about 1 mg to about 1 gram.

17. A process according to claim 16 wherein said alcohol oxidase is admixed with a binder.

18. A process according to claim 17 wherein said binder is one of acacia, gelatin, sucrose, methyl cellulose, alginic acid, or guar gum.

19. A process according to claim 16 wherein said alcohol oxidase is admixed with a diluent.

20. A process according to claim 19 wherein said diluent is one of lactose, starch, dibasic calcium phosphate or calcium sulfate.

21. A process according to claim 16 wherein said alcohol oxidase is admixed with a disintegrating agent.

22. A process according to claim 21 wherein said disintegrating agent is one of starch, alginic acid, microcrystalline cellulose, cross-linked providone or collodial silicates.

23. A process according to claim 16 wherein said alcohol oxidase is within an enteric coating suitable to slow down its inactivation in the stomach.

24. A process for reducing the alcohol content of human blood wherein alcohol oxidase, present in amounts from about 1-200 mg/mL of tonic, is administered to a recipient in the form of a tonic in an amount of from 1 to 50 mL.

25. A process according to claim 24 wherein niacin is admixed with said alcohol oxidase.

26. A compositions suitable for injection into the human body which comprises the enzyme alcohol oxidase present in an injectable solution in an amount sufficient to reduce the level of alcohol in human blood.

27. A composition according to claim 26 suitable for injection into the human body which comprises the enzyme alcohol oxidase present in either an aqueous or a isotonic saline solution.

28. A composition according to claim 27 further comprising an oxygen carrier.

29. A composition according to claim 28 further comprising an antioxidant.

30. A composition according to claim 29 wherein said antioxidant is one of ascorbic acid, ascorbyl palmitate, monothioglycerol or sodium bisulfite.

31. A composition according to claim 28 wherein said alcohol oxidase is attached to either dextran or polyethylene glycol.

32. A composition in tablet form suitable for oral consumption which comprises the enzyme alcohol oxidase in an amount sufficient to reduce the level of alcohol in the blood and a binder.

33. A composition according to claim 32 in the form of a tablet wherein said alcohol oxidase is present in an amount ranging from about 1 mg to about 1 g per tablet.

34. A composition according to claim 33 further comprising a diluent.

35. A composition according to claim 34 further comprising a disintegrating agent.

36. A composition according to claim 35 further comprising a lubricant.

37. A composition according to claim 36 which has an enteric coating suitable to diminish inactivation of said alcohol oxidase by the stomach.

38. A composition in the form of a tonic suitable for oral administration comprising alcohol oxidase present in an aqueous solution in an amount of about 2-200 mg per ml and sufficient to reduce the level of alcohol oxidase in human blood.

39. A composition according to claim 38 wherein said alcohol oxidase is present in an amount of from about 1-200 mg of alcohol oxidase per ml of tonic solution.

* * * * *